(12) United States Patent
Clark et al.

(10) Patent No.: US 8,685,729 B2
(45) Date of Patent: Apr. 1, 2014

(54) HETEROLOGOUS EXPRESSION OF EXTREMOPHILE HEAT SHOCK PROTEINS AND CHAPERONES IN MICROORGANISMS TO INCREASE TOLERANCE TO TOXIC COMPOUNDS

(75) Inventors: Douglas S. Clark, Orinda, CA (US); Timothy Whitehead, Berkeley, CA (US); Frank T. Robb, Gaithersburg, MD (US); Pongpan Laksanalamai, Baltimore, MD (US); Anchalee Jiemjit, Baltimore, MD (US)

(73) Assignees: The Regents of the University of California, Oakland, CA (US); University of Maryland, Baltimore, Baltimore, MD (US)

( * ) Notice: Subject to any disclaimer, the term of this patent is extended or adjusted under 35 U.S.C. 154(b) by 467 days.

(21) Appl. No.: 12/528,620

(22) PCT Filed: Feb. 26, 2008

(86) PCT No.: PCT/US2008/054978
§ 371 (c)(1),
(2), (4) Date: Nov. 12, 2010

(87) PCT Pub. No.: WO2008/106430
PCT Pub. Date: Sep. 4, 2008

(65) Prior Publication Data
US 2011/0045554 A1 Feb. 24, 2011

Related U.S. Application Data

(60) Provisional application No. 60/903,341, filed on Feb. 26, 2007.

(51) Int. Cl.
| | | |
|---|---|---|
| *C12N 5/00* | (2006.01) | |
| *C12N 1/00* | (2006.01) | |
| *C12N 1/20* | (2006.01) | |
| *C12N 15/74* | (2006.01) | |
| *C12Q 1/02* | (2006.01) | |
| *C12P 21/06* | (2006.01) | |
| *C12P 7/06* | (2006.01) | |
| *C12P 7/16* | (2006.01) | |
| *C07K 1/00* | (2006.01) | |
| *C07H 21/04* | (2006.01) | |

(52) U.S. Cl.
USPC ............ 435/375; 435/29; 435/69.1; 435/160; 435/161; 435/252.33; 435/254.22; 435/243; 435/471; 530/350; 536/23.7

(58) Field of Classification Search
None
See application file for complete search history.

(56) References Cited

U.S. PATENT DOCUMENTS 5,827,685 A * 10/1998 Lindquist .................... 435/69.1
6,579,699 B1   6/2003 Kikuchi
6,960,465 B1  11/2005 Papoutsakis

FOREIGN PATENT DOCUMENTS

WO    WO 2007/022419 A2   2/2007

OTHER PUBLICATIONS

Robb et al. heat shock proteins in hyperthermophiles, Methods in Microbiology (2006), 35: 233-252.*
Liao et al. An ethanol inducible alc system for regulating gene expression in *Beauveria bassiana*, World Journal of Microbiology and Biotechnology, (Nov. 2009), vol. 25, Issue 11, pp. 2065-2069, Epub Jul. 9, 2009.*
Boonyaratanakornkit et al., "Transcriptional profiling of hyperthermophilic methanarchaeon *Methanococcus jannaschii* in response to lethal heat and non-lethal cold shock," 2005,Environmental Microbiology, 7(6), 789-797.
International Search Report for corresponding International Application No. PCT/US2008/054978, filed Feb. 26, 2008.
Laksanalamai et al., "Minimal Protein-Folding Systems in Hyperthermophilic Archaea," Apr. 2004, Nature Reviews Microbiology, vol. 2, No. 4; 315-324.
Laksanalamai et al., "Small heat shock proteins from extremophiles: a review," 2004, Extremophiles, 8:1-11.
Tomas et al., "Overexpression of *groESL* in *Clostridium acetobutylicum* Results in Increased Solvent Production and Tolerance, Prolonged Metabolism, and Changes in the Cell's Transcriptional Program," Aug. 2003, Applied and Environmental Microbiology, vol. 69, No. 8, 4951-4965.
Whitehead et al., "A filamentous molecular chaperone of the prefoldin family from the deep-sea hyperthermophile *Methanocaldococcus jannaschii*," 2007, Protein Science, 16: 626-634.

* cited by examiner

*Primary Examiner* — Iqbal H Chowdhury
(74) *Attorney, Agent, or Firm* — Kilpatrick Townsend & Stockton LLP

(57) ABSTRACT

The invention provides methods and compositions for increasing tolerance of microorganisms to toxic agents, such as solvents; and for increasing production of solvents from solvent-generating microorganisms. The methods comprise engineering a microorganism of interest to express a heterologous heat-shock protein/chaperone, e.g., Group II chaperonin or a prefoldin such as γ-prefoldin, where the heterologous protein is from an extremophile, such as an archaean.

16 Claims, 6 Drawing Sheets

HETEROLOGOUS EXPRESSION OF EXTREMOPHILE HEAT SHOCK PROTEINS AND CHAPERONES IN MICROORGANISMS TO INCREASE TOLERANCE TO TOXIC COMPOUNDS

CROSS-REFERENCES TO RELATED APPLICATIONS

This application is the U.S. National Stage entry of International Application No. PCT/US2008/54978, filed Feb. 26, 2008, which claims benefit of U.S. provisional application No. 60/903,341, filed Feb. 26, 2007, which are herein incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under National Science Foundation (NSF) Grant Nos. BES-0224733 and MCB 9809352, and National Institutes of Health (NIH) Grant No. T32 GM08352. The Government has certain rights to this invention.

BACKGROUND OF THE INVENTION

Microorganisms can produce chemical compounds that range from solvents to lipids and other compounds that have industrial use. Such a compound may, however, itself have toxic effects on the microorganism that produces the compound. Furthermore, the microorganism may be able to produce only a relatively small amount of the chemical compound, thus limiting the commercial use of the microorganism as a biological source of the chemical compound.

This invention addresses the need for strategies to improve the ability of microorganisms to produce commercially important chemical compounds that may otherwise be toxic to the organism.

BRIEF SUMMARY OF THE INVENTION

The present invention is based on the discovery that expression of genes encoding heterologous heat shock proteins from extremophiles in microorganisms enhances tolerance to toxic compounds, e.g., organic solvents, and improves yield of the toxic compounds. Thus, in one aspect, the invention provides a method of increasing the tolerance of a microorganism to a toxic agent, the method comprising introducing a nucleic acid sequence encoding a heat shock protein from an extremophile into the microorganism and expressing the nucleic acid sequence, whereupon the microorganism has increased tolerance when exposed to the toxic agent. In another aspect, the invention also provides a method of obtaining a toxic compound from a microorganism, the method comprising: expressing a heterologous nucleic acid sequence encoding a heat shock protein from an extremeophile in the microorganism; culturing the microorganism for a sufficient time under conditions that allows production of the toxic compound; and harvesting the toxic compound, wherein the amount of toxic compound produced by the microorganism is increased in comparison to a microorganism that does not express the heat shock protein.

In some embodiments, the heat shock protein is a chaperone. For example, the chaperone can be a Group II chaperonin, e.g., thermosome. In other embodiments, the chaperone is a prefoldin, such as γ prefoldin.

In some embodiments, the nucleic acid sequence is operably linked to an inducible promoter, in other embodiments, the nucleic acid sequence is linked to a constitutive promoter.

In some embodiments, the extremophile that is the source of the heat shock protein, a Group II chaperonin or a prefoldin such as γ prefoldin, is an *Archaeal* species, e.g., a *Methanocaldococcus* species. In other embodiments, the extremophile that is the source of the heat shock protein is from a species of bacteria, yeast, cyanobacteria, or filamentous fungi.

In some embodiments, the microorganism that is engineered to increase tolerance to a chemical compound and/or production of the chemical compound is a bacteria e.g., a *Clostridium* species, or *Escherichia coli* (*E. coli*) or *Zymomonas mobilis*. In some embodiments, the bacteria, e.g., *E. coli*, comprises heterologous genes that encode solvent-producing enzymes.

In other embodiments the microorganism into which the extremophile heat shock protein is introduced is a yeast, a filamentous fungus, a microalgae, a cyanobacterium, or an *Archaeal* species.

The method often comprises introducing the extremophile heat shock protein into a microorganism that produces a toxic compound that is an organic solvent. In some embodiments, the microorganism produces a toxic compound that is ethanol, butanol, a longer chained alcohol, a terpene, an alkane, a fatty acid, a fatty acid ester e.g., biodiesel, or a ketone, e.g., acetone.

In a further aspect, the invention provides a microorganism that comprises an expression vector comprising a heterologous nucleic acid sequence encoding γ prefoldin. The microorganism can be a bacteria species, a yeast, an *archaeal* species, a filamentous fungus, a microalgae, or a cyanobacteria species. In some embodiments, the microorganism is a bacteria, e.g., *E. coli*, a species of *Clostridium*, e.g., *Clostridium acetobutylicum* or *Clostridium beyerinckii*, *Zymomonas mobilis*, a species of *Lactobacillus*, a species of *Bacillus*, *Corynebacteria glutamicum*, or *Brevibacterium flavum*. In other embodiments, the microorganism is a yeast, e.g., *Saccharomyces cervisae*, *Candida albicans*, or *Pichia pastoris*. In further embodiments, the microorganism is a filamentous fungus, e.g., *Aspergillus* or *Neurospora*.

The invention further provides a method of increasing the resistance of a microorganism to lethal heat, the method comprising introducing an expression cassette comprising a heterologous nucleic acid encoding γ prefoldin into the microorganism.

In an additional aspect, the invention provides a massculture vessel comprising a population of microorganisms that produces a toxic compound where the microroganims have been modified to express an extremeophile heat shock protein in accordance with the invention. In some embodiments, the microorganism expresses a Group II chaperonin, e.g., thermosome from an *Archaeal* species, or a prefoldin, such as γ prefoldin from an *Archaeal* species. In some embodiments, the microorganism produces an organic solvent. In some embodiments, the toxic compound produced by the microorganism is ethanol, butanol, a longer chain alcohol such as a 5-carbon alcohol, a terpene, an alkane such as octane, a fatty acid, a fatty acid ester, or ketone, e.g., acetone.

DETAILED DESCRIPTION OF THE INVENTION

Figure 1:
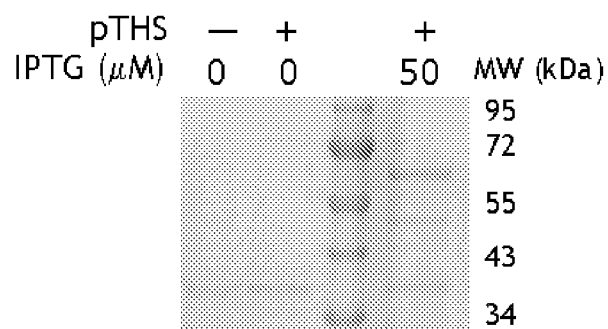
FIG. 1 provides exemplary data showing expression of thermosome in TUNER pCodonPlus *E. coli* cells. The thermosome was subcloned into a pET19 vector. Expression was confirmed after 4 hr when grown aerobically in 4 g/L glucose in M9 minimal media.

This invention relates to the discovery that genes encoding heat shock proteins, e.g., chaperones, that are from extremophiles can be used to engineer microorganisms that have increased tolerance to toxic agents, such as solvents. Thus, heat shock proteins such as thermosome or γ-PFD from extremophiles may be used to increase the production of toxic compounds, such as organic solvents, from microorganisms.

DEFINITIONS

A "heat shock protein" in the context of this invention refers to a protein that belong in a class of proteins that were first identified as up-regulated in response to stress, heat. A "heat shock protein" assists in correct protein folding, intracellular protein localization, and other functions in the cell to maintain protein structure and function. Stress protein are grouped into families according to their molecular mass. "Heat shock proteins" for use in the invention include Hsp 70 (DNA K) proteins, which have a molecular weight from about 65-80 kDa; Hsp 60 proteins (chaperonins), which have a molecular weight from about 55-64 kDa, Hsp 40 (family members, which have a molecular weight of about 35-54, and small Hsp proteins, which have a molecule weight of less than about 35 kDa. In some embodiments, large molecular weight heat shock proteins, e.g., Hsp 90 proteins, may be employed.

Heat shock proteins as broadly defined herein encompass chaperones, including chaperones that are not up-regulated in response to heat or other stress.

A "chaperone" in the context of this invention refers to a protein that binds to misfolded or unfolded polypeptide chains and affects the subsequent folding processes of the chains. A hallmark of a "chaperone" is the ability to prevent aggregation of normative proteins. For a review of chaperones, see, e.g., Hartl and Hayer-Hartl, *Science* 295:1852-1858, 2002). As used herein, "chaperonins" refers to a subgroup of "chaperones" that are structurally related and share a stacked ring structure. Chaperonins assist, in an ATP-dependent manner, in the efficient folding of polypeptides. Chaperonins are found in bacteria, archaea, and eukarya and form double-ring toroidal structures with seven to nine subunits of 60 kDa per ring. Each ring encloses a central cavity for the binding of a non-native protein. Two class of chaperonins, Group I and Group II, have been defined, which are similar in overall structure, but do not share substantial sequence homology. Group I chaperonins are typically found in the bacterial cytosol, mitochondria, and chloroplasts, although they have also been identified in *Archaea* as well (e.g., in *Methanosacrcina* species). Group II chaperonins commonly occur in the *archaeal* and eukaryotic cytosol. For a review of chaperonins, see, e.g., The Chaperonins, R. J. Ellis, ed. (San Diego, Calif., Academic Press, 1996).

A "Group II chaperonin" typically occurs in *Archaea* and in the eukaryotic cytosol. A Group II chaperonin is a toroidal, ATP-dependent chaperone that is characterized by the presence of identical or divers subunits arranged in rings of eight or nine subunits. Typically, Group II chaperonins have two eight- or nine-membered rings that are composed of two types of subunits in the case of *Archaeal chaperonins* or eight different subunits in the case of the eukaryotic chaperonin containing TCP-1 (CCT). Group II chaperonins, in *Archaea*, e.g., thermophilic or hyperthermophilic *Archaea*, are also often referred to as "thermosome" (Phipps et al., *Nature* 361: 475-477, 1993, Klumpp & Baumesister, *FEBS Letters* 430: 73-77, 1998). Structural analyses of Group II chaperonins are available in the art (see, e.g., *J Struct Biol.* 135:147-56, 2001; *J Mol Biol.* 336:717-29, 2004 and references cited therein). Chaperonins include an ATPase domain, an intermediate domain, and a substrate-binding domain. Group II chaperonins from eukaryotic cytosol are referred to as "TCP1," which identifies one of the proteins comprising the ring structure, "TriC", which is an abbreviation for TCP1 ring chaperonin, or "CCT", which is an abbreviation for chaperonin containing TCP1.

A "prefoldin" in the context of this invention refers to a type of chaperone that is typically characterized by a heterohexameric molecular structure that has been referred to as jellyfish-like. Prefoldins are found in all Eurkayotes and *Archaea*. Prefoldins have traditionally been grouped into two main evolutionarily related classes: one class that has 140 residues (a prefoldin) and a second class that as 120 residues (β prefoldin). The crystal structure of prefoldin from an *Archaeal* species has been solved (e.g., Siegert et al., *Cell* 103:621-632, 2000). The term "prefoldin" encompasses homologs to α and β prefoldin, e.g., γ prefoldin, that do not associate with either α and β prefoldin to form heteroligomeric complexes. The term "γ prefoldin" (also referred to herein as "γ PFD" or "γ-PFD") refers to an *Archaeal* prefoldin homolog that was first identified in *Methanocaldococcus jannaschii*. "γ prefoldin" forms long filaments of identical subunits.

An "extremophile" in the context of this invention refers to an organism that exhibits optimal growth under extreme environment conditions. Extremophiles include acidophiles, alkaliphiles, halophiles, thermophiles (including hyerthermophiles, which are typically found in an environment that has a temperature of above 80° C.), metalotolerant organisms, osmophiles, and xerophiles.

An "organic solvent" as used herein refers to a carbon-containing solution that dissolves solid, liquid or gaseous solutes. In the context of this invention, an organic solvent at sufficient concentrations can reduce cell viability and/or proliferation when present in the environment of a microorganism. In some embodiments, the organic solvent is also produced by the microorganism. Organic solvents produced by microorganisms include alcohols, e.g., ethanol and butanol; ketones, e.g., acetone, and alkanes, e.g., octane.

A "toxic" compound in the context of this invention refers to a compound that when present at a high level can induce irreversible damage to a microorganism. "Toxic" compounds as used herein includes organic solvents, including alcohols, e.g., ethanol and butanol and longer chain alcohols such as 5-carbon alcoholes; terpenes, e.g., amorpha-4,11-diene; alkanes, e.g., octane; fatty acids, e.g., palmitic acid; fatty acid esters, e.g., palmitic acid methyl ester; and ketones, e.g., acetone.

A "bioreactor" or "mass-culture vessel" in the context of this invention is any enclosed large-capacity vessel in which bacteria, yeast, and other microorganisms are grown. A "large-capacity vessel" in the context of this invention can hold about 100 liters, often about 500 liters, or about 1,000 liters to about 1,000,000 liters, or more.

As used herein, "harvesting" a toxic compound produced by a microorganism, e.g., an organic solvent such as ethanol, butanol, acetone, etc., refers to capturing and sequestering such compounds in a closed or contained environment.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell.

A chaperone (or other heat shock protein) "gene", e.g., a prefoldin gene such as γ PFD gene, or a Group II chaperonin gene, such as a thermosome gene, in the context of this invention refers to a nucleic acid that encodes the chaperone (or heat shock protein), or fragment thereof. Often, such a "gene" is a cDNA sequence that encodes the protein.

"Expression" of a heterologous heat shock protein gene, e.g., a gene encoding a chaperone such as prefoldin or a chaperonin such as Group II chaperonin, refers to an increase in level of the heat shock protein encoded by the gene in a microorganism in comparison to a control microorganism of the same species that has not been transduced with an expression vector encoding the heat shock protein.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as a heat shock protein gene or chaperonin gene, wherein the expression control sequence directs transcription of the nucleic acid corresponding to the second sequence.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants An "expression cassette" refers to a nucleic acid construct, which when introduced into a host cell, results in transcription and/or translation of a RNA or polypeptide, respectively.

In the case of expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "gene", e.g., a γ-PFD or Group II chaperonin gene.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window", as used herein, includes reference to a segment of any one of the number of contiguous positions, e.g., 20 to 600, usually about 50 to about 200, more usually about 100 to about 150 in which a sequence may be compared to a reference sequence of the same number of contiguous positions after the two sequences are optimally aligned.

The term "substantial identity" in the context of polynucleotide or amino acid sequences means that a polynucleotide or polypeptide comprises a sequence that has at least 50% sequence identity to a reference sequence. Alternatively, percent identity can be any integer from 50% to 100%. Exemplary embodiments include at least: 55%, 57%, 60%, 65%, 70%, 75%, 80%, 85%, 90%, 95%, or 99% identity compared to a reference sequence using the programs described herein; preferably BLAST using standard parameters, as described below. Accordingly, γ-PFD sequences include nucleic acid sequences that have substantial identity to SEQ ID NO:1 or SEQ ID NO:3. A, γ-PFD polypeptide sequence of the invention includes polypeptide sequences having substantial identify to SEQ ID NO:2 or SEQ ID NO:4.

Polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. For example, γ prefoldin polynucleotides, can also be identified by their ability to hybridize under stringency conditions (e.g., Tm ~40° C.) to nucleic acid probes having the sequence of SEQ ID NO:1 or SEQ ID NO:3. Such a nucleic acid sequence can have, e.g., about 25-30% base pair mismatches or less relative to the selected nucleic acid probe. SEQ ID NO:1 is an exemplary γ prefoldin polynucleotide sequence. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest.

As used herein, "mass-culturing" refers to growing large quantities of a microorganism, e.g., for the production of a solvent such as ethanol. A "large quantity" is generally in the range of about 100 liters to about 1,500,000 liters, or more. In some embodiments, the organisms are cultured in large quantities in modular bioreactors, each having a capacity of about 1,000 to about 1,000,000 liters.

Extremophile Heat Shock Protein Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999 with updates through 2007).

In some embodiments, the chaperone or heat shock protein is from *Archaea*. There are many *Archaea* known, including members of the genera *Pyrococcus, Thermococcus, Thermoplasma, Thermotoga, Sulfolobus, Halobacterium*, and methanogens, e.g., *Methanocaldococcus, Methanococcus, Methanothermabacteria*; and variohalobacterium. Examples of *Archaea* include *Pyrococcus furiosus; Pyrococcus horikoshii, Sulfolobus solfataricus, Sulfolobus acidocaldarius, Sulfolobus brierleyi, Sulfolobus hakonensis, Sulfolobus metallicus, Sulfolobus shibatae, Aeropyrum pernix; Archaeglobus fulgidus; Thermoplasma acidophilum; Thermoplasma volcanium, Thernotoga maritime, Methanocaldococcus jannaschii; Methanobacterium thermoautotrophicum, Haloferax volcanii*, and *Halobacterium* species NRC-1.

Extremophilic bacteria, including *Thermus* sp. and *Bacillus* sp. may also be used as a source of heat shock protein or chaperone that is used in the invention. Thermophilic *Bacillus* sp. include *B. stearothermophilus; B. calvodex; B. caldotenax, B. thermoglucosidasius, B. coagulans, B. licheniformis, B. thermodenitrificans*, and *B. caldolyticus*.

In some embodiments, a heat shock protein or chaperone for use in this invention is from a eukaryotic extremophile, e.g., a yeast. Examples of extremophilic yeast include *Trichosporon* species, *Hansenula* species, *Candida* species, *Arxiozyma* species, and the like.

In further embodiments, the heat shock protein may be from an extremophilic fungus, such as a thermophilic fungus. For a reviews, see, e.g., Maheshwari, et al., *Microbiology and Molecular Biology Reviews* 64:461-488, 2000.

Extremophilic blue green algae, i.e., cyanobacteria, are also known. Such cyanobacteria include *Synechococcus* sp and *Mastigocladus* sp.

The heat shock protein may be any heat shock protein from an extremophile, e.g., Hsp90, Hsp70, Hsp60, Hsp40, or low molecular weight heat shock proteins. See, for example, a review of low molecular weight heat shock proteins from Extremophiles. (Laksanalamai & Robb, *Extremophiles* 8:1-11, 2004) or Laksanalamai, et al., (*Nature Reviews Microbiol.* 2:315-324, 2004) for a review of protein-folding systems in hyperthermophilic *Archaea*.

In some embodiments, the heat shock protein is a chaperone, e.g., a chaperonin. The chaperonin may be a Group I or Group II chaperonin.

In exemplary embodiments, heterologous heat shock proteins, e.g., chaperone proteins such as prefoldins and Group II chaperonins, for use in this invention are from *Archaea*. Archaeal heat shock proteins have been identified in various *Archaea*. For a review, see, e.g., Robb et al., pp. 209-223, in *Archaea: Molecular and Cellular Biology*, Cavicchiolo, ed. ASM Press, 2007).

In some embodiments, the heat shock protein is a Group II chaperonin from *Archaea*. Group II chaperonins are also commonly referred to as "thermosome". The majority of Group II chaperonins in *Archaea* have eight subunits per ring (e.g., Klumpp & Baumeister *FEBS Letters* 430:73-77, 1998), but the chaperonins in the thermoacidophilic *Archaea* in the family Sulfolobales have nine subunits per ring (Trent et al., *Nature* 354:490-493, 1991; Marco et al., *FEBS* 341: 152-155, 1994). These *Sulfolobus* octadecameric chaperonins are often referred to as "rosettasomes" (Kagawa et al., *J. Mol. Biol.* 253: 712-725, 1995).

An exemplary Group II chaperonin for use in this invention is the *M. jannaschii* thermosome sequence (which is available under accession number MJ_0999). Other examples of thermosomes include chaperonins from *Pyrodictium occultum, Thermoplasma acidophilum* and *Methanopyrus kandleri* (Ellis et al., *J. Struc. Biol.* 123:30-36, 1998). Still other thermosome genes can be obtained from *Nitrosopumilus maritimus, Methanococcus maripaludis, Pyrobaculum islandicum, Pyrobaculum calidifontis. Methanoregula boonei, Methanococcus aeolicus, Methanosaeta thermophila, Methanosarcina mazei*, and *Pyrococcus furiosus*, among many others.

In some embodiments, the heat shock protein is a prefoldin. The prefoldin may be an α, β, or γ PFD. Exemplary prefoldins include γ prefoldin, e.g., SEQ ID NOs:2 and 4.

A gene encoding a prefoldin for use in the invention can be from any extremophile. In some embodiments, the prefoldin is from an *Archaeal* species, e.g., from *Methanocaldococcus, Methanobacterium, Aquifex aeolicus* or *Pyrococcus*. The prefoldin may be an α, β, or γ PFD. Exemplary prefoldins include γ prefoldin, e.g., SEQ ID NOs:2 and 4.

Isolation of Extremophile Heat Shock Protein Genes

Isolation or generation of heat shock/chaperone polynucleotides can be accomplished by a number of techniques. Cloning and expression of such technique will be addressed in the context of thermosome and γ PFD genes. However, the same techniques can be used to isolate and express other heat shock proteins and chaperones from extremeophiles. For instance, nucleic acid probes based on known sequences or the exemplary γ prefoldin and thermosome sequences disclosed here can be used to identify the desired polynucleotide in a cDNA or genomic DNA library from a desired extremophile species. Probes may be used to hybridize with genomic DNA or cDNA sequences to isolate homologous genes in a same or different species.

In typical embodiments, the nucleic acids of interest from extremophile can be amplified from nucleic acid samples using amplification techniques. For instance, PCR may be used to amplify the sequences of the genes directly from mRNA, from cDNA, from genomic DNA, or from libraries.

Appropriate primers and probes for identifying a heat shcok protein gene such as a thermosome or γ PFD gene from an extremophiles, e.g., *Archaea*, can be generated from comparisons of the sequences provided herein and from sequences available in the art. For a general overview of PCR see PCR Protocols: A Guide to Methods and Applications. (Innis, M, Gelfand, D., Sninsky, J. and White, T., eds.), Academic Press, San Diego (1990).

Preparation of Recombinant Vectors

To express the extremophile sequences, e.g., Group II chaperonin and prefoldin sequences such as γ PFD or thermosome, recombinant DNA vectors suitable for transformation of the organism of interest, e.g., a bacteria, a yeast, an *archaeal* species, a microalgae species, or a microscopic filamentous fungus, are prepared. Techniques for transformation are well known and described in the technical and scientific literature. For example, a DNA sequence encoding a γ PFD gene or a thermosome gene, can be combined with transcriptional and other regulatory sequences which will direct the transcription of the sequence from the gene in the intended cells, e.g., bacteria, yeast, and the like. In some embodiments, an expression vector that comprises an expression cassette that comprises the heat shock protein or chaperone gene further comprises a promoter operably linked to the gene. In other embodiments, a promoter and/or other regulatory elements that direct transcription of the gene are endogenous to the microorganism, e.g., yeast, and the expression cassette comprising the heat shock protein or chaperone gene is introduced, e.g., by homologous recombination, such that the heterologous heat shock protein or chaperone gene is operably linked to an endogenous promoter and is expression driven by the endogenous promoter.

Regulatory sequences include promoters, which may be either constitutive or inducible. In some embodiments, a promoter can be used to direct expression of a heat shock protein or a chaperones under the influence of changing environmental conditions. Examples of environmental conditions that may effect transcription by inducible promoters include the presence of a solvent such as ethanol, anaerobic conditions, elevated temperature, or the presence of light. Promoters that are inducible upon exposure to chemicals reagents are also used to express nucleic acids encoding a heat shock protein or chaperone. Other useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Skerra, *Gene* 151:131-135, 1994; and Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449, 1991); an ethanol inducible promoter (Felenbok, *J. Biotech.* 17:11-18, 1991), or an arabinose promoter (Guzman et al., *J. Bacteriol.* 177:4121-4130, 1995). In some embodiments, a promoter that is inducible by the toxic compound, e.g., an ethanol-inducible promoter, is used for the expression of the heterologous extremophile heat shock protein.

One of skill in the art understands that in some embodiments, it may be desirable to time the induction of expression of the heterologous extremophile heat shock protein or chaperone. Accordingly, expression may be induced early during growth or at later stages of growth of the microorganism. For example, in some embodiments, expression of a gene may be induced up to four hours after exponential growth to two hours before the end of the growth phase.

In other embodiments, expression of the heat shock protein or chaperone may be induced by the presence of a toxic compound using a promoter that is inducible by the compound. For example, expression of the heat shock protein may be induced by the presence of an organic solvent such as ethanol when an ethanol-inducible promoter is employed.

In yeast, a number of vectors containing constitutive or inducible promoters may be used. See for example, Current Protocols in Molecular Biology, Ausubel, supra Grant, et al., 1987. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Other examples of promoters suitable for use in yeast include CYC1, HIS3, PGK, PHO5, GAPDH, ADC1, TRP1, URA3, ENO, TPI (e.g., useful for expression in *Saccharomyces*) and AOX1 (e.g., useful for expression in *Pichia*). Alternatively, vectors may be used which promote integration of foreign DNA sequences into the yeast chromosome.

Promoters that can be used in non-yeast fungi, e.g., microscopic filamentous fungi such as *Neurospora* or *Aspergillus*, include promoters from the β-tubulin gene, the grg-1 gene, invertase, and the like. Teachings on transforming filamentous fungi are reviewed in U.S. Pat. No. 5,741,665 and in U.S. Pat. No. 5,695,965. Additional techniques as applied to *Neurospora crassa* are found, for example in Davis and de Serres, *Methods Enzymol* 17A:79-143, 1971. Further teachings on transforming filamentous fungi are reviewed in U.S. Pat. No. 5,674,707. Gene expression in filamentous fungi has additionally been reviewed in Punt et al. *Trends Biotechnol* 20:200-6, 2002, Archer & Peberdy Crit. Rev Biotechnol (1997) 17(4):273-306.

Additional examples of expression systems and transformation of yeast and fungi can be found, e.g., in U.S. Patent Application Publication Nos. 2007/0196449 and 20060257923.

A vector comprising a Group II chaperonin or prefoldin nucleic acid sequences will typically comprise a marker gene that confers a selectable phenotype on the cell to which it is introduced. Such markers are known. For example, the marker may encode antibiotic resistance, such as resistance to kanamycin, G418, bleomycin, hygromycin, and the like.

The thermosome or prefoldin sequence of the invention are expressed recombinantly in an organism of interest, e.g., bacteria, yeast, microalgae, cyanobacteria, filamentous fungi, or an *archaeal* species. As appreciated by one of skill in the art, expression constructs can be designed based on parameters such as codon usage frequencies of the organism in which the nucleic acid is to be expressed. Codon usage frequencies can be tabulated using known methods (see, e.g., Nakamura et al. *Nucl. Acids Res.* 28:292, 2000). Codon usage frequency tables are also available in the art e.g., in codon usage databases such as the database developed and maintained by Yasukazu Nakamura at The First Laboratory for Plant Gene Research, Kazusa DNA Research Institute, Japan).

Microorganisms that can be Targeted

In accordance with the invention, an extremophile heat shock protein can be expressed in any number of microorganisms where it is desirable to enhance tolerance to, and in some embodiments increase production of, a toxic compound such as an organic solvent, or another compound that can be toxic to the microorganism. The toxic compound may be produced naturally by the microorganism or can be produced as a result of genetic engineering. In some embodiments of the invention, the toxic compound may be generated as a result of a fermentation process, with the proviso that the toxic compound is not a amino acid that is produced by the organism.

In embodiments in which the toxic compound is an organic solvent, the organic solvent may be produced by fermentation or by non-fermentative pathways (see, e.g., Atsumi et al., *Nature* 451:86-89, 2008).

In some embodiments, the heat shock protein is expressed in a bacteria. The bacteria can be any bacteria that is typically exposed to a toxic compound, or that produces a toxic compound. In some embodiments, the bacteria produce an organic solvent, e.g., ethanol, butanol, or acetone. Particularly useful in the present invention will be cells that are readily adaptable to large-scale culture for production of industrial quantities of the toxic compound. Such organisms are well known in the art of industrial bioprocessing, examples of which may be found in Recombinant Microbes for Industrial and Agricultural Applications, Murooka et al., eds., Marcel Dekker, Inc., New York, N.Y. (1994), and include fermentative bacteria as well as yeast and filamentous fungi. Host cells can includes, e.g., *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Serratia* sp., *Rhizobium* sp., and *Streptomyces* sp., *Zymomonas mobilis*, acetic acid bacteria, methylotrophic bacteria, *Propionibacterium, Acetobacter, Arthrobacter, Ralstonia, Gluconobacter, Propionibacterium*, and *Rhodococcus*.

In some embodiments, the microorganism produces an organic solvent. For example, species of *Clostridium* are known that produced acetone or butanol. Thse include *Clostridium acetobutylicum, Clostridium beijericki* and related species, e.g, *Clostridium cellulolyticum, Clostridium thermocellum, Clostridium butyricum*, and *Clostridium saccharoperbutylacetonicum*. In other embodiments, *Zymomonas mobilis* may be modified in accordance with the invention to express an extremophile heat shock protein or chaperone such as a prefoldin, e.g., γ prefoldin or Group II chaperonin, e.g., thermosome.

In some embodiments, the microorganism is engineered to produce a solvent, e.g., ethanol or butanol (see, e.g., U.S. Pat. No. 5,424,202; WO/2008/006038; Atsumia, et al., *Metab Eng.* 2007 Sep. 14, 2007; Atsumi et al., *Nature* 451:86-89, 2008).

In some embodiments, the microorganism into which the heat shock protein is introduced is a yeast that produces a toxic compound, e.g., an organic solvent. A yeast that may be modified in accordance with the invention includes yeast that have been genetically engineered to produced a toxic compound. For example, yeast have been modified for carotenoid production (Shimada et al, *Applied and Environmental Microbiology* 64:2676-2680, 1998) and to produce artemisinic acid (Ro et al, *Nature* 440:940-943, 2006)

Among the genera of filamentous fungi that can be modified to express a heat shock protein from an extremophile are *Aspergillus, Neurospora, Chrysosporium, Thielavia, Neurospora, Aureobasidium, Filibasidium, Piromyces, Cryplococcus, Acremonium, Tolypocladium, Scytalidium, Schizophyllum, Sporotrichum, Penicillium, Gibberella, Myceliophthora, Mucor, Fusarium, Humicola*, and *Trichoderma*.

In some embodiments, an *archaeal* species may be additionally modified with a heterologous heat shock protein in order to increase tolerance and/or production of a toxic compound.

In other embodiments, a microalgae or cyanobacteria may be modified in accordance with the invention to express an extremophile heat shock protein, e.g., a Group II chaperonin or a prefoldin. Examples of microalge include species of *Dunaliella, Chlamydomonas*, and *Chlorella*. Examples of cyanobacteria include *Synechocystis* sp.

Cell transformation methods and selectable markers for bacteria, yeast, cyanobacteria, filamentous fungi and the like are well known in the art, and include electroporation, ballistic method, as well as chemical transformation methods.

Conditions for growing bacteria, yeast, or other microorganisms that express a heat shock protein from an extremophile, e.g., a Group II chaperonin, such as thermosome or γ-prefoldin for the exemplary purposes illustrated above are known in the art (see, e.g., the exemplary references cited herein). Compounds produced by the modified microorganisms can be harvested using known techniques. For example, compounds that are not miscible in water may be siphoned off from the surface and sequestered in suitable containers.

In typical embodiments, transformed microorganisms that express a heterologous heat shock protein gene are grown under mass culture conditions for the production of the toxic compound, e.g., an organic solvent. The transformed organisms are grown in bioreactors or fermentors that provide an enclosed environment to contain the toxic compound. In typical embodiments for mass culture, the transformed cells are grown in enclosed reactors in quantities of at least about 500 liters, often of at least about 1000 liters or greater, and in some embodiments in quantities of about 1,000,000 liters or more.

EXAMPLES

Example 1

Figure 4:
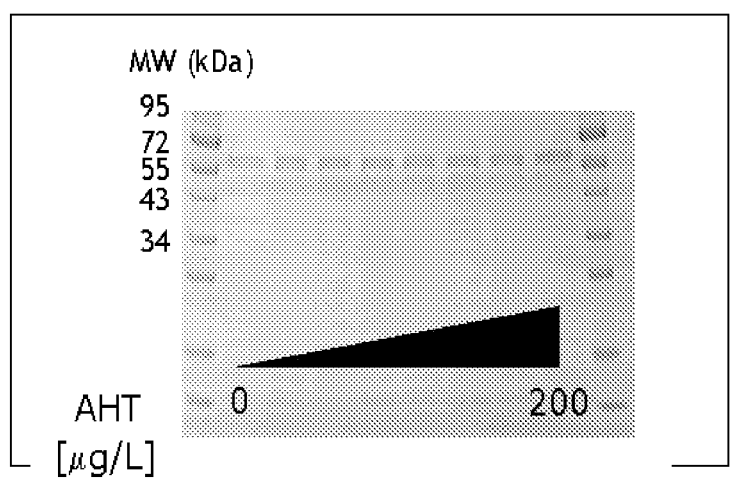

Enhancement of Survival and Solvent Tolerance of E. coli Cells Expressing Thermosome A nucleic acid encoding thermosome from *Methanocaldococcus jannaschii* was expressed in two strains of *E. coli* (TUNER pCodonPlus and the ethanologenic strain KO11). For expression of thermosome in TUNER pCodonPlus cells, the thermosome polynucleotide was subcloned into a pET19 vector, which has an inducible promoter such that the thermosome gene is expressed in the presence of IPTG. Expression was confirmed after 4 hr when the cells were grown aerobically in 4 g/L glucose in M9 minimal media. The electrophoresis results (FIG. 1) confirm expression of the thermosome in TUNER pCodonPLus cells. For expression of thermosome in KO11 *E. coli* cells, codon-optimized thermosome was subcloned into vector pASK33+, which enables induction in the presence of anhydrotetracycline (AHT). Expression was confirmed after 24 hr when grown anaerobically in 100 g/L glucose, 1×LB and varying concentrations of AHT (FIG. 4).

Figure 2:
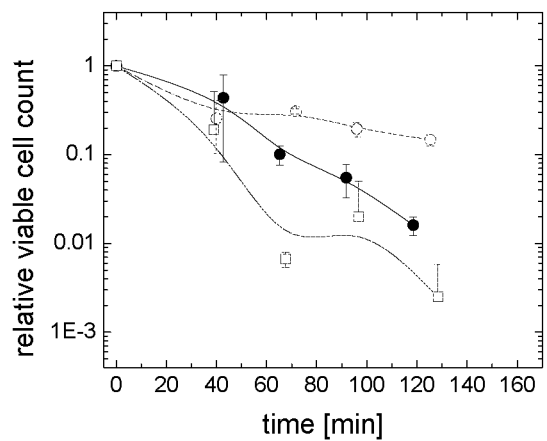
FIG. 2 provides exemplary data showing relative viable cell count as a function of incubation time in the presence of 82 g/L ethanol TUNER pCodonPlus cells were grown aerobically in 4 g/L glucose and M9 minimal salts media until $OD_{595}$=0.4, at which point they were removed and incubated in growth media containing 82 g/L ethanol. The plasmid pET-TERM encodes a variant of γ prefoldin that does not form filaments, and thus is not a molecular chaperone, which is used as an expression control, closed black circles, TUNER pCodonPlus; open circles, TUNER pCodonPlus pET-THS with 50 μM IPTG; open squares, TUNER pCodonPlus pET-TERM with 50 μM IPTG FIG. 3 provides exemplary data showing relative viable cell count as a function of incubation time in the presence of 86 g/L ethanol TUNER pCodonPlus cells were grown aerobically in 4 g/L glucose and M9 minimal salts media until $OD_{595}$=0.4, at which point they were removed and incubated in growth media containing 86 g/L ethanol closed black circles, TUNER pCodonPlus; open circles, TUNER pCodonPlus pET-THS with 50 μM IPTG; open squares, TUNER pCodonPlus pET-TERM (expression control) with 50 μM IPTG FIG. 4 provides exemplary data showing the expression of thermosome in KO11. Codon-optimized thermosome was subcloned in pASK33+ vector. Expression was confirmed after 24 hr when grown anaerobically in 100 g/L glucose, 1×LB and varying concentrations of AHT.
Figure 3:
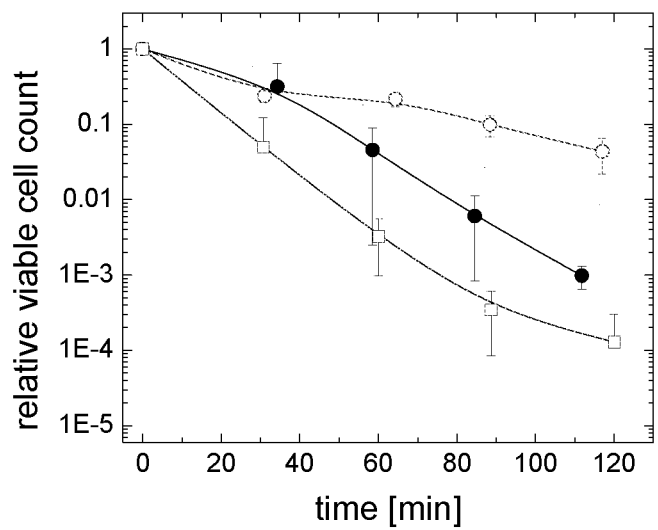
Figure 5:
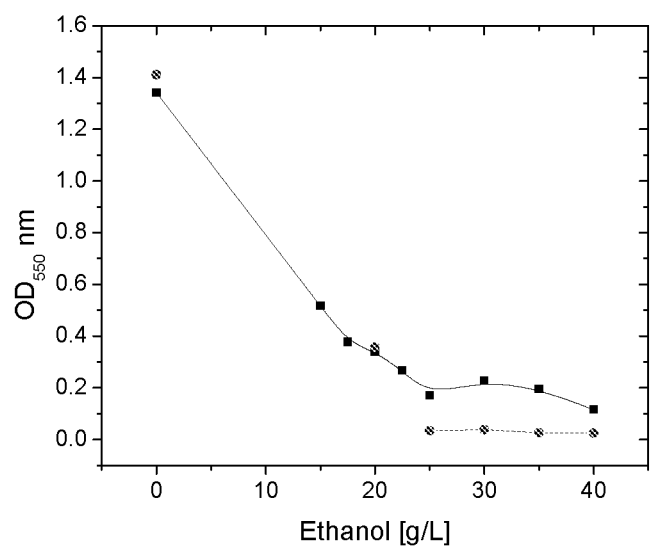
FIG. 5 provides exemplary data showing the effect of ethanol on growth of KO11 strains in the presence of ethanol. All samples were inoculated at $OD_{550}$=0.1 and grew for 48 h at 30° C. in 100 g/L glucose, 1×NBS media with 1 mM betaine, pH uncontrolled, squares, KO11 pTHS (with 200 μg/L AHT); circles, KO11 pASK33+

Survivability of cells expressing the heterologous thermosome was compared to control cells that do not express the thermosome. For the experimental results depicted in FIG. 2, relative viable cell count was determined as a function of incubation time in the presence of 82 g/L ethanol TUNER pCodonPlus cells were grown aerobically in 4 g/L glucose and M9 minimal salts media with 50 μM IPTG until $OD_{595}=0.4$, at which point the cells were removed and incubated in growth media containing 82 g/L ethanol FIG. 3 shows the relative viable cell count as a function of incubation time in the presence of 86 g/L ethanol TUNER pCodonPlus cells were grown aerobically in 4 g/L glucose and M9 minimal salts media until $OD_{595}=0.4$, at which point they were removed and incubated in growth media containing 86 g/L ethanol. The results show that thermosome expression enhances the survivability of cells upon exposure to ethanol Cells expressing thermosome were also analyzed for the ability to grow in the presence of ethanol in comparison to control cells that did not express thermosome. FIG. 5 shows that thermosome expression enhances the ability of cells to grow in the presence of ethanol. For the data depicted in FIG.

5, KO11 cells were inoculated at $OD_{550}$=0.1 and grew for 48 h at 30° C. in 100 g/L glucose, 1×NBS media with 1 mM betaine, pH uncontrolled.

Thermosome-expressing KO11 *E. coli* cells, with produce ethanol, were also evaluated for ethanol production in comparison to control cells that did not express thermosome. The data in Tables 1 and 2 show that thermosome expression increased ethanol production.

TABLE 1

Summary of KO11 fermentations on complex growth medium. Fermentations were carried out for 72 h in 2x LB, pH 6.0, containing 140 g/L glucose as the growth medium. The pH of was controlled by 2N KOH addition.

| | | Strain | | | | |
|---|---|---|---|---|---|---|
| | | KO11 | KO11 | KO11pTHS** | KO11pTHS** | KO11pTHS* |
| | | | | Replicate | | |
| | | 1 | 2 | 1 | 2 | 1 |
| Initial glucose concentration | [g L$^{-1}$] | 140 | 140 | 140 | 140 | 140 |
| Residual glucose concentration | [g L$^{-1}$] | 16 | 14 | 22 | 20 | 0 |
| Max cell concentration | [g L$^{-1}$] | 2.25 | 2.04 | 1.98 | 2.07 | 2.14 |
| Final Ethanol Concentration | [g L$^{-1}$] | 53 | 53 | 39 | 39 | 61 |
| Ethanol yield (g EtOH/g glucose consumed) | [g g–1] | 0.43 | 0.42 | 0.33 | 0.33 | 0.44 |

*Induction with 200 μg/L anhydrotetracycline at start of fermentation compared to in starter culture
**Induction with 200 μg/L anhydrotetracycline in starter culture

TABLE 2

Summary of KO11 fermentations in minimal growth medium. Fermentations were carried out for 50 h in NBS minimal salts medium, pH 7.0, containing 100 g/L glucose. The pH was controlled with 2N KOH addition.

| | | Strain | | | |
|---|---|---|---|---|---|
| | | KO11 | KO11 | KO11pTHS* | KO11pTHS* |
| | | | | Replicate | |
| | | 1 | 2 | 1 | 2 |
| Initial glucose concentration | [g L$^{-1}$] | 100 | 100 | 100 | 100 |
| Residual glucose concentration | [g L$^{-1}$] | 46 | 41 | 0 | 11 |
| Max cell concentration | [g L$^{-1}$] | 0.68 | 0.61 | 1.15 | 0.99 |
| Final Ethanol Concentration | [g L$^{-1}$] | 9 | 5 | 14 | 17 |
| Ethanol yield (g EtOH/g glucose consumed) | [g g–1] | 0.17 | 0.08 | 0.14 | 0.19 |

*Induction with 200 μg/L anhydrotetracycline at start of fermentation

Example 2

Characterization of Recombinant *Methanococcus jannaschii* Gamma-Prefoldin (γ-PFD)

A transcript of an open reading frame of *Methanocaldococcus jannaschii* was identified as being significantly up-regulated in response to a lethal heat shock (Boonyaratanakornkit, et al., *J. Environ. Microbiol.* 7:289-797, 2005). The gene was obtained from genomic *Methanocaldococcus jannaschii* and expressed in *E. coli* to evaluate protein structure and function. Examination of γ-PFD by transmission electron microscopy showed that γ-PFD forms long filaments of definable dimensions. γ-PFD does not associate with either α or β PFD to form hetero-oligomeric complexes. γ-PFD is also remarkably stable. Its secondary structure is stable up to at least 100° C. and its filamentous structure resists denaturation in 7M guanidinium chloride, which is a treatment that unfolds almost all polypeptides. Further analysis demonstrated that γ-PFD exhibits activity as a molecular chaperone. For example, γ-PFD stabilized citrate synthase, an aggregation-prone enzyme, at 45° C. at a 5:1 monomer-to-monomer stoichiometric ratio, and greatly reduced aggregation at a 2:1 ratio. γ-PFD was also co-incubated with a chemically denatured GFP variant at 30° C. Fluorescence measurements showed that GFP refolding increased with increasing concentration of γ-PFD, illustrating that γ-PFD can function as a refolding chaperone in the absence of ATP.

Example 3

Enhanced Heat and Solvent Tolerance in *E. coli* Expressing Recombinant *Methanococcus jannaschii* γ-PFD A nucleic acid encoding γ-PFD was amplified from genomic *Methanococcus jannaschi* and subcloned into various *E. coli* cells in order to evaluated the effects of expression of γ-PFD on tolerance to ethanol. The genes was ligated into a pET19b vector and transformed into the *E. coli* Rosetta strain (Novagen). Control Rosetta cells were transformed with vector alone. The prefoldin expression was induced with IPTG using known methodology.

In one experiment, increased tolerance to heat was evaluated. Control and γ PFD-expressing strains of *E. coli* were diluted to an $OD_{600}$ of 0.2 and 0.6, respectively. Aliquots were shifted to 50° C. The viability of the cells was evaluated up to 120 minutes by measuring colony forming unit (CFU) measurements. The expression of γ PFD resulted in a one-thousand fold protection of E. coli cells exposed to 50° C. for 120 minutes.

Figure 6:
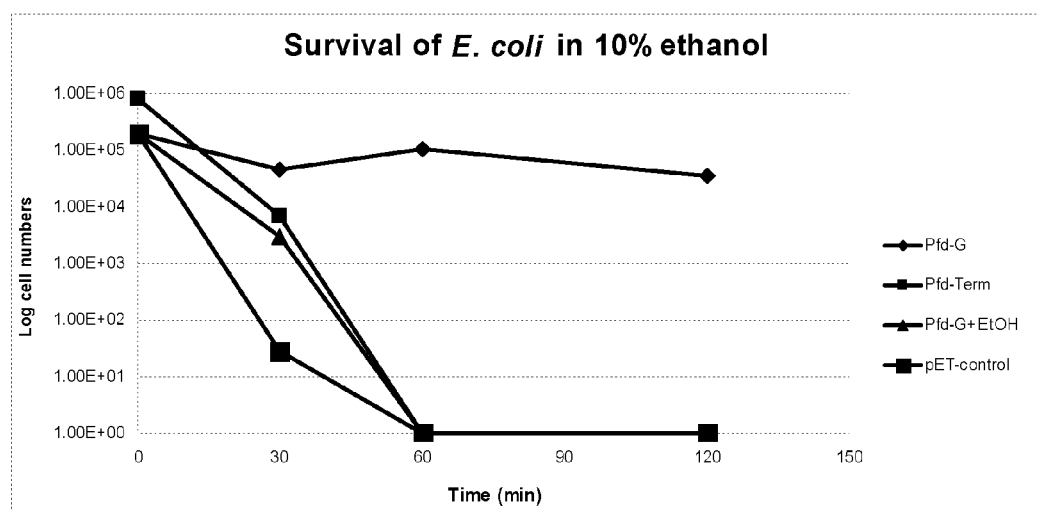
FIG. 6 proves exemplary data showing enhanced heat and solvent tolerance of *E. coli* that express *Methanococcus jannaschii* gamma-Prefoldin (γ-PFD).

Protection by γ-PFD against the combined lethal effects of 5% ethanol and 50° C. was tested. In FIG. 6, diamonds indicate survival of Mj-γ-PFD-expressing E. coli Rosetta at 50° C. in the absence of ethanol. The large squares indicate the survival of the control E. coli Rosetta strain in 5% (v/v) ethanol at 50° C. Cells were induced at an OD600 of 0.4 by addition of 1 mM IPTG. Ethanol was added to the culture at 37° C., and the cultures were immediately transferred to a shaking water bath at 50° C. for the times indicated. The triangles show the survival of E. coli expressing Mj-γ-PFD at 50° C. in 5% ethanol. The small squares indicate the survival of E. coli expressing the TERM mutant Mj-γ-PFD, to be compared with the wild type Mj-γ-PFD (diamonds). The results show that the E. coli that express Mj-γ-PFD exhibit enhanced survival when exposed to ethanol and high temperatures.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

Exemplary Sequences

SEQ ID NO:1 M. jannaschii γ prefoldin nucleic acid sequence

ATGGTAAATGAAGTCATAGACATAAATGAAGCAGTTAGAGCATACATA

GCTCAAATTGAAGGTTTGAGAGCTGAAATTGGAAGATTAGACGCAACA

ATAGCAACATTGAGACAGTCATTAGCAACATTAAAGAGCTTAAAAACA

TTGGGAGAGGGGAAAACTGTCTTAGTTCCTGTTGGAAGTATTGCTCAA

GTAGAGATGAAAGTTGAAAAGATGGATAAGGTTGTTGTTTCAGTTGGA

CAGAATATTTCAGCTGAGTTAGAGTATGAGGAGGCATTGAAATACATT

GAAGATGAAATTAAAAAGCTATTGACATTCAGATTAGTCTTAGAGCAA

GCAATTGCCGAATTGTATGCAAAAATAGAGGATTTAATTGCAGAAGCT

CAACAAACATCTGAAGAAGAAAAGCAGAAGAGGAAGAAAATGAAGAA

AAAGCTGAATAA

SEQ ID NO:2 M. jannaschii γ prefoldin polypeptide sequence.

MVNEVIDINEAVRAYIAQIEGLRAEIGRLDATIATLRQSLATLKSLKT

LGEGKTVLVPVGSIAQVEMKVEKMDKVVVSVGQNISAELEYEEALKYI

EDEIKKLLTFRLVLEQAIAELYAKIEDLIAEAQQTSEEEKAEEEENEE

KAE

SEQ ID NO:3 Aquifex aeolicus γ prefoldin nucleic acid sequence

ATGGCAGAAGAGAAGAAGGAAGTTCAAAAAACTCCTGAGCAAAAAATG

GATGAGCTAAACAGACAGCTCAGGGGTTACATGGCTAACATTGAAGCC

CTCAGGGCTGAAATTTCCGTTATCAATCAATCCATAACGGACCTCAGA

ACCGCAGAAGCTACTCTAAGAAGCTTAAAGGAACTCGGAAAGGGTAAA

GAAGTGCTCATACCCGTAGGAGCTACCGCACAGATAAAGGCAAAGAGT

GAAGGCGTTGACGAGGTGATAATGAGCATAGGAACGGGAATATCCGCG

GTAATGAGCTACGACGAGGCGGTAGACAGGATAAGAAAGGAAATAGCA

GCTCTGGAAGCTCTAAGGAGGGCACTTGAGGAAGCGATAGCCGATCTC

TACAACAAAATTGAAGAACTTCTCGAAGAAGTAAGA420AAAGTTGGA

CAGGAGGAGGCTAAAAAATAA

SEQ ID NO:4 Aquifex aeolicus γ prefoldin polypeptide sequence

MAEEKKEVQKTPEQKMDELNRQLRGYMANIEALRAEISVINQSITFTD

LRTAEATLRSLKELGKGKEVLIPVGATAQIKAKSEGVDEVIMSIGTGI

SAVMSYDEAVFTDRIRKEIAALEALRRALEEAIADLYNKIEELLEEVR

KVGQEEAKK

SEQ ID NO:5 M. jannaschii thermosome nucleic acid sequence: MJ_0999

ATGGCAATGGCAGGAGCACCAATAGTAGTATTACCACAAAACGTTAAG

AGATACGTTGGAAGAGATGCTCAAAGAATGAACATCTTAGCAGGTAGA

ATTATCGCTGAAACAGTTAGAACAACATTAGGTCCAAAAGGAATGGAC

AAAATGTTAGTTGATGAGTTAGGAGACATTGTTGTTACAAACGATGGA

GTTACAATATTAAAAGAAATGAGTGTTGAGCACCCAGCTGCTAAGATG

TTAATAGAAGTTGCTAAAACCCAAGAAAAAGAAGTTGGAGATGGAACA

ACAACAGCAGTTGTTATTGCTGGAGAGTTGTTAAGAAAAGCTGAAGAG

TTGTTAGACCAAAACATCCACCCATCAGTCATCATCAACGGATACGAA

ATGGCAAGAAACAAAGCAGTTGAAGAATTAAAGTCAATAGCTAAAGAA

GTTAAGCCAGAAGACACAGAGATGTTAAAGAAAATTGCAATGACATCA

ATTACTGGTAAAGGAGCAGAGAAAGCAAGAGAACAGTAGCTGAAATTG

TTGTTGAGGCAGTTAGAGCTGTTGTTGATGAAGAAACTGGAAAAGTTG

ATAAGGACTTAATTAAAGTTGAGAAGAAAGAAGGAGCTCCAATTGAAG

AAACCAAGTTAATTAGAGGAGTTGTTATTGACAAAGAGAGTCAACC

CACAAATGCCAAAGAAAGTTGAAAACGCTAAGATTGCATTATTAAACT

GCCCAATTGAAGTCAAAGAAACAGAGACAGATGCAGAAATAAGAATTA

CTGACCCAGCTAAGTTAATGGAGTTCATTGAGCAAGAAGAGAAGATGA

TTAAAGACATGGTTGAGAAGATTGCTGCTACAGGAGCAAATGTAGTAT

TCTGTCAGAAAGGAATTGATGACTTAGCTCAGCACTACTTAGCTAAGA

AGGGAATCTTAGCAGTAAGAAGAGTTAAAAAAATCAGACATGGAAAAAT

-continued

```
TAGCTAAAGCAACAGGAGCAAGAATCGTTACAAAGATTGACGACTTAA
CACCAGAGGACTTAGGAGAAGCTGGATTAGTTGAAGAGAGAAAAGTTG
CTGGAGATGCAATGATATTCGTCGAGCAGTGCAAGCATCCAAAGGCTG
TAACAATCTTAGCAAGAGGTTCAACAGAGCACGTTGTTGAAGAAGTTG
CAAGAGCAATTGATGATGCAATTGGAGTTGTTAAGTGTGCATTAGAAG
AAGGTAAGATTGTTGCTGGTGGGGAGCAACTGAAATAGAATTAGCTA
AGAGATTAAGAAAATTCGCTGAGTCAGTTGCTGGAAGAGAACAGTTAG
CAGTTAAAGCATTCGCTGATGCTTTAGAAGTCATTCCAAGAACATTAG
CTGAAAACTCAGGATTAGACCCAATTGACATGCTCGTTAAGTTAAGAG
CTGCTCACGAGAAAGAAGGCGGAGAAGTCTATGGATTAGATGTCTTCG
AAGGAGAAGTTGTCGATATGTTAGAGAAAGGAGTTGTTGAACCATTGA
AAGTTAAAACACAAGCTATTGACTCAGCTACAGAGGCATCAGTCATGC
TCTTAAGAATCGATGACGTCATAGCTGCTGAGAAAGTTAAAGGAGACG
AAAAAGGAGGAGAAGGAGGAGACATGGGAGGGGATGAATTTTAA
```

SEQ ID NO:6 *M. jannaschii* thermosome polypeptide sequence:

```
MAMAGAPIVVLPQNVKRYVGRDAQRMNILAGRIIAETVRTTLGPKGMD
KMLVDELGDIVVTNDGVTILKEMSVEHPAAKMLIEVAKTQEKEVGDGT
TTAVVIAGELLRKAEELLDQNIHPSVIINGYEMARNKAVEELKSIAKE
VKPEDTEMLKKIAMTSITGKGAEKAREQLAEIVVEAVRAVVDEETGKV
DKDLIKVEKKEGAPIEETKLIRGVVIDKERVNPQMPKKVENAKIALLN
CPIEVKETETDAEIRITDPAKLMEFIEQEEKMIKDMVEKIAATGANVV
FCQKGIDDLAQHYLAKKGILAVRRVKKSDMEKLAKATGARIVTKIDDL
TPEDLGEAGLVEERKVAGDAMIFVEQCKHPKAVTILARGSTEHVVEEV
ARAIDDAIGVVKCALEEGKIVAGGGATEIELAKRLRKFAESVAGREQL
AVKAFADALEVIPRTLAENSGLDPIDMLVKLRAAHEKEGGEVYGLDVF
EGEVVDMLEKGVVEPLKVKTQAIDSATEASVMLLRIDDVIAAEKVKGD
EKGGEGGDMGGDEF
```

What is claimed is:

1. A method of increasing the tolerance of a microorganism to a toxic compound, the method comprising introducing an expression cassette comprising a nucleic acid sequence encoding a heterologous γ prefoldin from an extremophile into the microorganism and expressing the nucleic acid sequence to produce γ-prefoldin, whereupon the microorganism has increased tolerance when exposed to the toxic compound.

2. The method of claim 1, wherein the γ prefoldin is from an *Archaea* species.

3. The method of claim 2, wherein the *Archaea* sp. is a *Methanocaldococcus* species.

4. The method of claim 1, wherein the extremophile is a species of bacteria, an *Archaeal* species, a species of yeast, or a *cyanobacteria* species.

5. The method of claim 1, wherein the microorganism is a species of bacteria, a species of yeast, a species of filamentous fungus, a species of cyanobacteria, or an *Archaeal* species.

6. The method of claim 5, wherein the bacteria is *Clostridium*, *Escherichia coli* (*E. coli*), or *Zymomonas mobilis*.

7. The method of claim 6, wherein the *E. coli* comprises heterologous genes that encode solvent-producing enzymes.

8. The method of claim 1, wherein the toxic compound is an organic solvent.

9. The method of claim 1, wherein the toxic compound is selected from the group consisting of ethanol, butanol, a five-carbon alcohol, a terpene, an alkane, a fatty acid, a fatty acid ester, and a ketone.

10. The method of claim 1, wherein the nucleic acid sequence in operably linked to an inducible promoter.

11. The method of claim 10, wherein the inducible promoter is a solvent inducible promoter.

12. The method of claim 1, wherein the nucleic acid sequence in operably linked to a constitutive promoter.

13. The method of claim 1, wherein the toxic agent to which the microorganism is exposed is produced by the microorganism.

14. A method of increasing the resistance of a microorganism to lethal heat, the method comprising introducing an expression cassette comprising a heterologous nucleic acid encoding γ prefoldin into the microorganism.

15. The method of claim 14, wherein the γ prefoldin is from an *Archaea* species.

16. The method of claim 15, wherein the *Archaea* sp. is a *Methanocaldococcus* species.

* * * * *

UNITED STATES PATENT AND TRADEMARK OFFICE
CERTIFICATE OF CORRECTION

PATENT NO. : 8,685,729 B2
APPLICATION NO. : 12/528620
DATED : April 1, 2014
INVENTOR(S) : Douglas S. Clark et al.

Page 1 of 1

It is certified that error appears in the above-identified patent and that said Letters Patent is hereby corrected as shown below:

In the Specification

Please cancel the text at Column 1, Line 21, through Line 25 and replace it with the following:
"This invention was made with government support under grant GM008352 awarded by the National Institutes of Health and under grants BES0224733 and MCB9809352 awarded by the National Science Foundation. The government has certain rights in the invention."

Signed and Sealed this
Tenth Day of October, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 444
<212> TYPE: DNA
<213> ORGANISM: Methanocaldococcus jannaschii
<220> FEATURE:
<223> OTHER INFORMATION: gamma-prefoldin (gamma-PFD) chaperone

<400> SEQUENCE: 1

```
atggtaaatg aagtcataga cataaatgaa gcagttagag catacatagc tcaaattgaa      60
ggtttgagag ctgaaattgg aagattagac gcaacaatag caacattgag acagtcatta     120
gcaacattaa agagcttaaa acattgggag aggggaaaa ctgtcttagt tcctgttgga     180
agtattgctc aagtagagat gaaagttgaa aagatggata aggttgttgt ttcagttgga     240
cagaatattt cagctgagtt agagtatgag gaggcattga aatacattga agatgaaatt     300
aaaaagctat tgacattcag attagtctta gagcaagcaa ttgccgaatt gtatgcaaaa     360
atagaggatt taattgcaga agctcaacaa acatctgaag aagaaaaagc agaagaggaa     420
gaaaatgaag aaaaagctga ataa                                          444
```

<210> SEQ ID NO 2
<211> LENGTH: 147
<212> TYPE: PRT
<213> ORGANISM: Methanocaldococcus jannaschii
<220> FEATURE:
<223> OTHER INFORMATION: gamma-prefoldin (gamma-PFD) chaperone

<400> SEQUENCE: 2

Met Val Asn Glu Val Ile Asp Ile Asn Glu Ala Val Arg Ala Tyr Ile
 1               5                  10                  15

Ala Gln Ile Glu Gly Leu Arg Ala Glu Ile Gly Arg Leu Asp Ala Thr
            20                  25                  30

Ile Ala Thr Leu Arg Gln Ser Leu Ala Thr Leu Lys Ser Leu Lys Thr
        35                  40                  45

```
Leu Gly Glu Gly Lys Thr Val Leu Val Pro Val Gly Ser Ile Ala Gln
         50                  55                  60

Val Glu Met Lys Val Glu Lys Met Asp Lys Val Val Ser Val Gly
 65                  70                  75                  80

Gln Asn Ile Ser Ala Glu Leu Glu Tyr Glu Glu Ala Leu Lys Tyr Ile
                 85                  90                  95

Glu Asp Glu Ile Lys Lys Leu Leu Thr Phe Arg Leu Val Leu Glu Gln
            100                 105                 110

Ala Ile Ala Glu Leu Tyr Ala Lys Ile Glu Asp Leu Ile Ala Glu Ala
            115                 120                 125

Gln Gln Thr Ser Glu Glu Lys Ala Glu Glu Glu Asn Glu Glu
        130                 135                 140

Lys Ala Glu
145
```

<210> SEQ ID NO 3
<211> LENGTH: 450
<212> TYPE: DNA
<213> ORGANISM: Aquifex aeolicus
<220> FEATURE:
<223> OTHER INFORMATION: gamma-prefoldin (gamma-PFD) chaperone

<400> SEQUENCE: 3

```
atggcagaag agaagaagga agttcaaaaa actcctgagc aaaaaatgga tgagctaaac    60
agacagctca ggggttacat ggctaacatt gaagccctca gggctgaaat ttccgttatc   120
aatcaatcca taacggacct cagaaccgca gaagctactc taagaagctt aaaggaactc   180
ggaaagggta agaagtgct catacccgta ggagctaccg cacagataaa ggcaaagagt    240
gaaggcgttg acgaggtgat aatgagcata ggaacgggaa tatccgcggt aatgagctac   300
gacgaggcgg tagacaggat aagaaaggaa atagcagctc tggaagctct aaggagggca   360
cttgaggaag cgatagccga tctctacaac aaaattgaag aacttctcga gaagtaaga    420
aaagttggac aggaggaggc taaaaaataa                                   450
```

<210> SEQ ID NO 4
<211> LENGTH: 153
<212> TYPE: PRT
<213> ORGANISM: Aquifex aeolicus
<220> FEATURE:
<223> OTHER INFORMATION: gamma-prefoldin (gamma-PFD) chaperone

<400> SEQUENCE: 4

```
Met Ala Glu Glu Lys Lys Glu Val Gln Lys Thr Pro Glu Gln Lys Met
 1               5                  10                  15

Asp Glu Leu Asn Arg Gln Leu Arg Gly Tyr Met Ala Asn Ile Glu Ala
            20                  25                  30

Leu Arg Ala Glu Ile Ser Val Ile Asn Gln Ser Ile Thr Phe Thr Asp
        35                  40                  45

Leu Arg Thr Ala Glu Ala Thr Leu Arg Ser Leu Lys Glu Leu Gly Lys
    50                  55                  60

Gly Lys Glu Val Leu Ile Pro Val Gly Ala Thr Ala Gln Ile Lys Ala
 65                  70                  75                  80

Lys Ser Glu Gly Val Asp Glu Val Ile Met Ser Ile Gly Thr Gly Ile
                 85                  90                  95

Ser Ala Val Met Ser Tyr Asp Glu Ala Val Phe Thr Asp Arg Ile Arg
            100                 105                 110

Lys Glu Ile Ala Ala Leu Glu Ala Leu Arg Arg Ala Leu Glu Glu Ala
            115                 120                 125
```

Ile Ala Asp Leu Tyr Asn Lys Ile Glu Glu Leu Leu Glu Glu Val Arg
    130                 135                 140

Lys Val Gly Gln Glu Glu Ala Lys Lys
145                 150

<210> SEQ ID NO 5
<211> LENGTH: 1628
<212> TYPE: DNA
<213> ORGANISM: Methanocaldococcus jannaschii
<220> FEATURE:
<223> OTHER INFORMATION: thermosome (ths) Group II chaperonin

<400> SEQUENCE: 5

| | | |
|---|---|---|
| atggcaatgg caggagcacc aatagtagta ttaccacaaa acgttaagag atacgttgga | 60 |
| agagatgctc aaagaatgaa catcttagca ggtagaatta tcgctgaaac agttagaaca | 120 |
| acattaggtc aaaaggaat ggacaaaatg ttagttgatg agttaggaga cattgttgtt | 180 |
| acaaacgatg gagttacaat attaaaagaa atgagtgttg agcacccagc tgctaagatg | 240 |
| ttaatagaag ttgctaaaac ccaagaaaaa gaagttggag atggaacaac aacagcagtt | 300 |
| gttattgctg gagagttgtt aagaaaagct gaagagttgt tagaccaaaa catccaccca | 360 |
| tcagtcatca tcaacggata cgaaatggca agaaacaaag cagttgaaga attaaagtca | 420 |
| atagctaaag aagttaagcc agaagacaca gagatgttaa agaaaattgc aatgacatca | 480 |
| attactggta aggagcaga gaaagcaaga gaacagtagc tgaaattgtt gttgaggcag | 540 |
| ttagagctgt tgttgatgaa gaaactggaa agttgataa ggacttaatt aaagttgaga | 600 |
| agaaagaagg agctccaatt gaagaaacca agttaattag aggagttgtt attgacaaag | 660 |
| agagagtcaa cccacaaatg ccaagaaaag ttgaaaacgc taagattgca ttattaaact | 720 |
| gcccaattga agtcaaagaa acagagacag atgcagaaat aagaattact gacccagcta | 780 |
| agttaatgga gttcattgag caagaagaga agatgattaa agacatggtt gagaagattg | 840 |
| ctgctacagg agcaaatgta gtattctgtc agaaaggaat tgatgactta gctcagcact | 900 |
| acttagctaa gaagggaatc ttagcagtaa gaagagttaa aaaatcagac atggaaaaat | 960 |
| tagctaaagc aacaggagca agaatcgtta caaagattga cgacttaaca ccagaggact | 1020 |
| taggagaagc tggattagtt gaagagagaa aagttgctgg agatgcaatg atattcgtcg | 1080 |
| agcagtgcaa gcatccaaag gctgtaacaa tcttagcaag aggttcaaca gagcacgttg | 1140 |
| ttgaagaagt tgcaagagca attgatgatg caattggagt tgttaagtgt gcattagaag | 1200 |
| aaggtaagat tgttgctggt gggggagcaa ctgaaataga attagctaag agattaagaa | 1260 |
| aattcgctga gtcagttgct ggaagagaac agttagcagt taaagcattc gctgatgctt | 1320 |
| tagaagtcat tccaagaaca ttagctgaaa actcaggatt agacccaatt gacatgctcg | 1380 |
| ttaagttaag agctgctcac gagaaagaag gcggagaagt ctatggatta gatgtcttcg | 1440 |
| aaggagaagt tgtcgatatg ttagagaaag gagttgttga accattgaaa gttaaaacac | 1500 |
| aagctattga ctcagctaca gaggcatcag tcatgctctt aagaatcgat gacgtcatag | 1560 |
| ctgctgagaa agttaaagga gacgaaaaag gaggagaagg aggagacatg ggaggggatg | 1620 |
| aattttaa | 1628 |

<210> SEQ ID NO 6
<211> LENGTH: 542
<212> TYPE: PRT
<213> ORGANISM: Methanocaldococcus jannaschii
<220> FEATURE:
<223> OTHER INFORMATION: thermosome (ths) Group II chaperonin

<400> SEQUENCE: 6

```
Met Ala Met Ala Gly Ala Pro Ile Val Val Leu Pro Gln Asn Val Lys
  1               5                  10                  15

Arg Tyr Val Gly Arg Asp Ala Gln Arg Met Asn Ile Leu Ala Gly Arg
             20                  25                  30

Ile Ile Ala Glu Thr Val Arg Thr Thr Leu Gly Pro Lys Gly Met Asp
         35                  40                  45

Lys Met Leu Val Asp Glu Leu Gly Asp Ile Val Thr Asn Asp Gly
     50                  55                  60

Val Thr Ile Leu Lys Glu Met Ser Val Glu His Pro Ala Ala Lys Met
 65                  70                  75                  80

Leu Ile Glu Val Ala Lys Thr Gln Glu Lys Glu Val Gly Asp Gly Thr
                 85                  90                  95

Thr Thr Ala Val Val Ile Ala Gly Glu Leu Leu Arg Lys Ala Glu Glu
            100                 105                 110

Leu Leu Asp Gln Asn Ile His Pro Ser Val Ile Ile Asn Gly Tyr Glu
        115                 120                 125

Met Ala Arg Asn Lys Ala Val Glu Glu Leu Lys Ser Ile Ala Lys Glu
    130                 135                 140

Val Lys Pro Glu Asp Thr Glu Met Leu Lys Lys Ile Ala Met Thr Ser
145                 150                 155                 160

Ile Thr Gly Lys Gly Ala Glu Lys Ala Arg Glu Gln Leu Ala Glu Ile
                165                 170                 175

Val Val Glu Ala Val Arg Ala Val Val Asp Glu Thr Gly Lys Val
            180                 185                 190

Asp Lys Asp Leu Ile Lys Val Glu Lys Lys Gly Ala Pro Ile Glu
        195                 200                 205

Glu Thr Lys Leu Ile Arg Gly Val Val Ile Asp Lys Glu Arg Val Asn
    210                 215                 220

Pro Gln Met Pro Lys Lys Val Glu Asn Ala Lys Ile Ala Leu Leu Asn
225                 230                 235                 240

Cys Pro Ile Glu Val Lys Glu Thr Glu Thr Asp Ala Glu Ile Arg Ile
                245                 250                 255

Thr Asp Pro Ala Lys Leu Met Glu Phe Ile Glu Gln Glu Glu Lys Met
            260                 265                 270

Ile Lys Asp Met Val Glu Lys Ile Ala Ala Thr Gly Ala Asn Val Val
        275                 280                 285

Phe Cys Gln Lys Gly Ile Asp Asp Leu Ala Gln His Tyr Leu Ala Lys
    290                 295                 300

Lys Gly Ile Leu Ala Val Arg Arg Val Lys Lys Ser Asp Met Glu Lys
305                 310                 315                 320

Leu Ala Lys Ala Thr Gly Ala Arg Ile Val Thr Lys Ile Asp Asp Leu
                325                 330                 335

Thr Pro Glu Asp Leu Gly Glu Ala Gly Leu Val Glu Glu Arg Lys Val
            340                 345                 350

Ala Gly Asp Ala Met Ile Phe Val Glu Gln Cys Lys His Pro Lys Ala
        355                 360                 365

Val Thr Ile Leu Ala Arg Gly Ser Thr Glu His Val Val Glu Glu Val
    370                 375                 380

Ala Arg Ala Ile Asp Asp Ala Ile Gly Val Val Lys Cys Ala Leu Glu
385                 390                 395                 400

Glu Gly Lys Ile Val Ala Gly Gly Gly Ala Thr Glu Ile Glu Leu Ala
                405                 410                 415
```

-continued

```
Lys Arg Leu Arg Lys Phe Ala Glu Ser Val Ala Gly Arg Glu Gln Leu
            420                 425                 430

Ala Val Lys Ala Phe Ala Asp Ala Leu Glu Val Ile Pro Arg Thr Leu
            435                 440                 445

Ala Glu Asn Ser Gly Leu Asp Pro Ile Asp Met Leu Val Lys Leu Arg
        450                 455                 460

Ala Ala His Glu Lys Glu Gly Gly Glu Val Tyr Gly Leu Asp Val Phe
465                 470                 475                 480

Glu Gly Glu Val Val Asp Met Leu Glu Lys Gly Val Val Glu Pro Leu
                485                 490                 495

Lys Val Lys Thr Gln Ala Ile Asp Ser Ala Thr Glu Ala Ser Val Met
            500                 505                 510

Leu Leu Arg Ile Asp Asp Val Ile Ala Ala Glu Lys Val Lys Gly Asp
            515                 520                 525

Glu Lys Gly Gly Glu Gly Gly Asp Met Gly Gly Asp Glu Phe
530                 535                 540
```